US00PP12175P2

(12) United States Plant Patent
Waterer et al.

(10) Patent No.: US PP12,175 P2
(45) Date of Patent: Oct. 30, 2001

(54) GERANIUM PLANT NAMED 'ROZANNE'

(75) Inventors: Gomer Donald Waterer; Rozanne Patricia Waterer, both of Bridgewater; Paul Gooderham, Diss, all of (GB)

(73) Assignee: Blooms of Bressingham, Ltd., Norfolk (GB)

( * ) Notice: Subject to any disclaimer, the term of this patent is extended or adjusted under 35 U.S.C. 154(b) by 0 days.

(21) Appl. No.: 09/257,301

(22) Filed: Feb. 25, 1999

(51) Int. Cl.[7] ..... A01H 5/00

(52) U.S. Cl. ..... Plt./324
(58) Field of Search ..... Plt./324

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of Geranium plant named 'Rozanne', characterized by its large single violet-blue flowers with white centers and purple-violet veins, profuse flowering, vigorous yet relatively low growth habit, deeply cut and divided green leaves, and its long flowering period beginning in mid-June and continuing into early November or the first frost.

2 Drawing Sheets

BACKGROUND OF THE INVENTION

The present invention relates to a new and distinct cultivar of hardy perennial herbaceous plant of the genus Geranium, a member of the Geraniaceae family, and known by the cultivar name 'Rozanne'.

This new cultivar originated from a cross carried out by inventors Gomer Waterer and Rozanne Waterer in Kilve, Bridgewater, Somerset, England. The seed parent was a cultivar of *Geranium wallichianum* referred to as 'Buxtons variety'. The pollen or male parent was an unnamed cultivar of *Geranium himalayense.*

The new cultivar was selected from the progeny of the stated cross by the inventors in Bridgewater, Somerset, England. Subsequent asexual reproduction by division performed by the inventor Paul Gooderham in Bressingham, England has established that the unique combination of characteristics as herein disclaimed for the new cultivar are fixed and retained through successive generations of asexual reproduction.

The new cultivar has not been observed under all possible environmental conditions. The phenotype may vary with variations in environment such as temperature, and light intensity without, however, any variance in the genotype.

BRIEF DESCRIPTION OF THE INVENTION

The following traits have been repeatedly observed and are determined to be basic characteristics of the new cultivar, which in combination distinguish the new cultivar from others:

1. Its compact bush clump habit produces profuse and continuous flowering in England from mid-June through early November or until the first frost.
2. Large, single violet-blue flowers with white centers and prominent purple-violet veins.
3. The deeply cut divided green leaves make a pleasing backdrop to the many large single violet-blue flowers.
4. The plant thrives best in full sun and well-drained soil, and does not grow well in dry shade conditions. The new cultivar is ideal for use in borders and containers.
5. Vigorous yet relatively low growth and flowering habit.

6. The flowers have a classic "crane's bill" shape which characterizes the genus.

The flowers of 'Rozanne' are similar in shape to the parent 'Buxtons Variety' (unpatented), but the large single violet-blue flowers with white centers and purple-violet veins distinguish from 'Buxtons Variety'. The leaves of 'Rozanne' resemble the leaves of the pollen parent both in shape and in the characteristic of retaining green foliage color well into the Autumn.

BRIEF DESCRIPTION OF THE PHOTOGRAPHS

Figure 1:
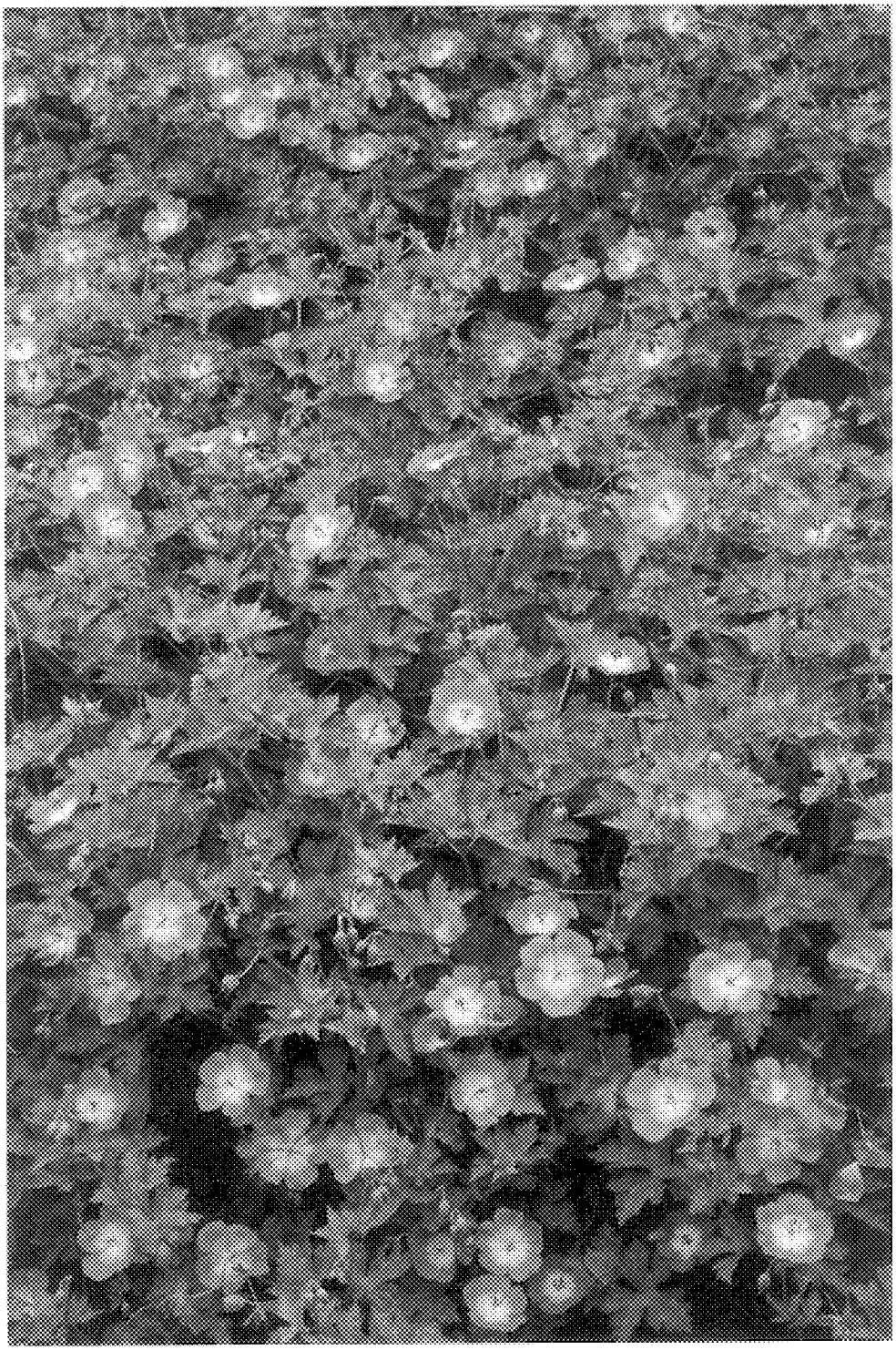

In the accompanying color photographs,

FIG. 1 comprises a front perspective view of plants of the new cultivar.

Figure 2:
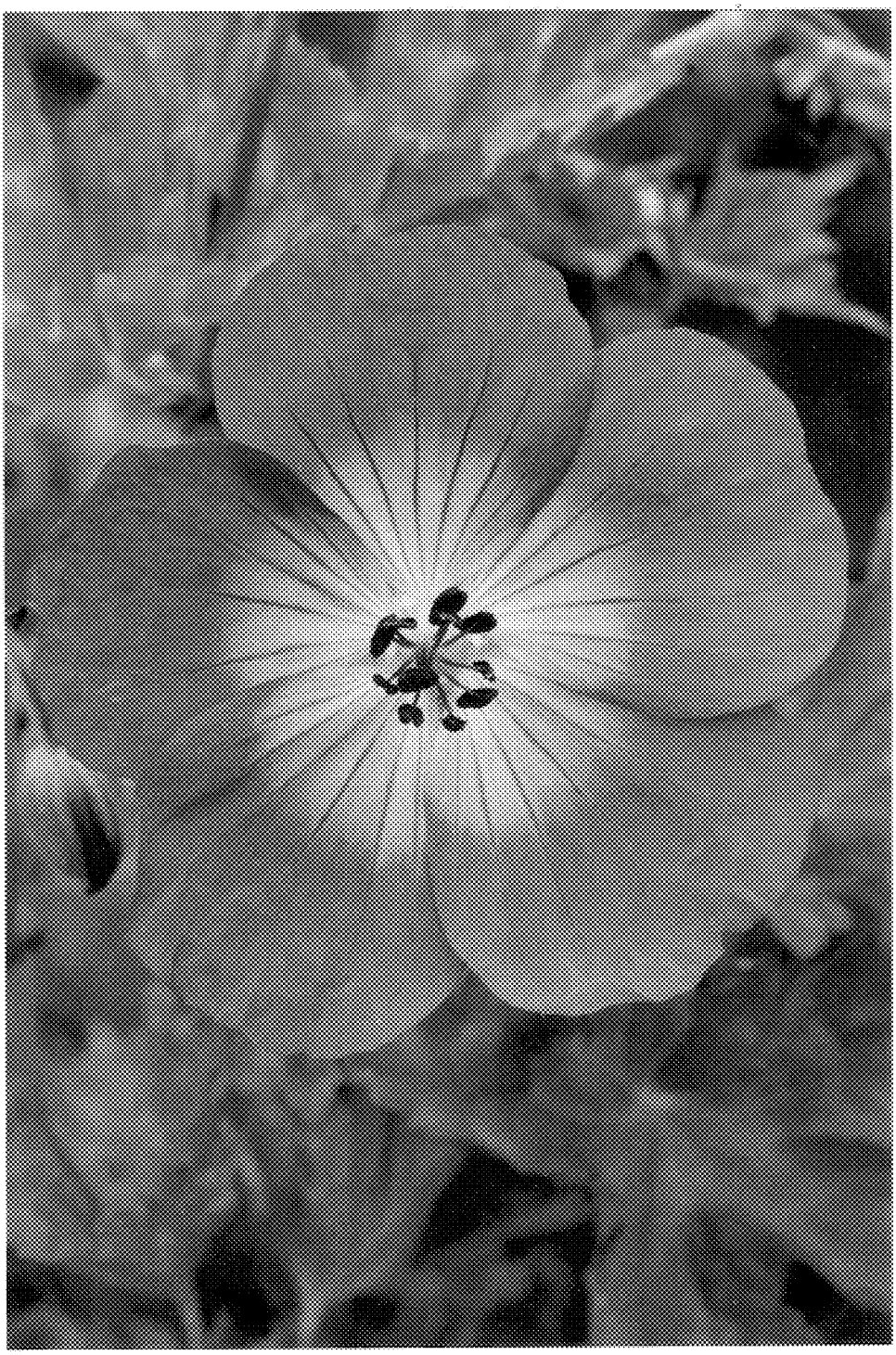

The photograph comprising FIG. 2 is a close-up view showing the single violet-blue flower with white center and purple-violet veins.

DETAILED BOTANICAL DESCRIPTION OF THE INVENTION

All color determinations and comparisons are based on The Royal Horticultural Society (R.H.S.) Colour Charts.

Plant:

*Origin.*—Seedling selection from *Geranium wallichianum* cv 'Buxton Variety' (seed parent) and a cultivar of *Geranium himalyense* (pollen parent).

*Type.*—Herbaceous perennial.

*Habit.*—Clump forming.

*Size.*—Mature plants are 40 cm in height with a spread of 60 cm.

*Root system.*—Fleshy.

*Plant vigor.*—A perennial that shows vigorous and healthy growth throughout Great Britain in British Isles climate.

*Blooming habit.*—Showy single violet-blue flowers are arranged in dichasial cymes.

*Blooming period.*—From mid-June continuing into early November or until the first frost.

*Hardiness.*—Winter hardy throughout the British Isles. The plant has not been fully tested for maximum summer tolerance about 32° C. (90° F.).

*Age.*—Beginning 2$^{nd}$ growing season.

*Growing conditions.*—Observed at Bressingham, England under normal conditions.

*Growth.*—Produced by tissue culture, it will divide every 4–6 weeks. Plants grown from plugs week 14 will have matured to 7.5 inches by week 32.

Flowers:

*Petals.*—Five veined petals of equal size per flower.

*Petal size.*—Length 25 mm.; Width 25 mm.

*Petal texture.*—Soft, silky.

*Petal shape.*—Heart-shaped.

*Flower shape.*—Bowl-shaped.

*Flower type.*—Cordate or triangular.

*Flower size.*—5 cm in diameter.

*Stamens.*—Anthers are absent from 1 every 4 flowers; they also drop off other flowers after approximately 5 days. There are 10 anthers per flower. Anther size is 3 mm. Anther color is purple RHS 79 A.

*Upper surface color.*—The main petal color of mature flowers is approximately 90A, with a much lighter transition area (92D) to a white center. The true main color is best shown in the flowers appearing near the bottom of FIG. 1. The veins are approximately 81A in color and are very prominent in the transition area and center.

*Lower surface color.*—Violet-blue RHS 90D.

*Sepal color.*—Upper side, green RHS 138 B; under side, green RHS 138A.

*Peduncle color.*—Yellow-green RHS 144 B with a slight red flush at flowering of RHS red 46 B.

Foliage:

*Arrangement.*—Leaves in pairs, 5 deeply cut lobed divisions.

*Texture.*—Both upper and lower surfaces are hairy.

*Whole leaf length.*—6 cm.

*Whole leaf width.*—9 cm.

*Petiole length.*—8 cm.

*Petiole color.*—RHS yellow-green 145 A to RHS red 46 B from late summer onwards.

*Margins.*—Parted.

*Apex.*—Acute.

*Base.*—Sagittate.

*Color.*—Mature leaves, upper surface 137A, under surface 138B; leaf margins have tint of red-purple 72A. Immature upper leaf surface, yellow-green RHS 144 A; immature under surface yellow-green RHS 146 C. Immature upper leaf surface, flushed red RHS 53 A.

Reproductive organs:

*Pistils.*—1, purple RHS 79 A.

*Fertility.*—Sterile.

*Seed.*—None.

*Fruit.*—None.

Pest and disease resistance: Typical of Geraniums, no observed disease resistance.

I claim:

1. A new and distinct cultivar of Geranium named 'Rozanne', as shown and described.

* * * * *